(12) United States Patent
Ritchie

(10) Patent No.: US 6,811,540 B1
(45) Date of Patent: Nov. 2, 2004

(54) ANKLE WRAPPING SYSTEM

(76) Inventor: Anthony L. Ritchie, 6316 S. Newland Ct., Littleton, CO (US) 80128

( * ) Notice: Subject to any disclaimer, the term of this patent is extended or adjusted under 35 U.S.C. 154(b) by 0 days.

(21) Appl. No.: 10/391,042

(22) Filed: Mar. 17, 2003

Related U.S. Application Data

(63) Continuation of application No. 09/564,487, filed on May 4, 2000, now Pat. No. 6,533,746.
(60) Provisional application No. 60/132,635, filed on May 5, 1999, now abandoned.

(51) Int. Cl.[7] .................................................. A61F 5/00
(52) U.S. Cl. .............................. 602/26; 602/65; 602/75; 128/882
(58) Field of Search ............................... 128/846, 869, 128/876, 882; 602/23, 26, 27, 60, 65, 75

(56) References Cited

U.S. PATENT DOCUMENTS

| | | | | |
|---|---|---|---|---|
| 958,199 A | * | 5/1910 | Wand | |
| 4,272,850 A | * | 6/1981 | Rule | 2/24 |
| 4,495,942 A | * | 1/1985 | Palumbo | 128/80 H |
| 4,705,025 A | * | 11/1987 | Dedo | 128/153 |
| 4,841,957 A | * | 6/1989 | Wooten | 128/80 H |
| 5,882,324 A | * | 3/1999 | Baranowski | 602/65 |
| 5,944,678 A | * | 8/1999 | Hubbard | 602/27 |
| 6,093,468 A | * | 7/2000 | Toms | 428/67 |
| 6,362,387 B1 | * | 3/2002 | Carlson | 602/41 |

* cited by examiner

Primary Examiner—Michael A. Brown
(74) Attorney, Agent, or Firm—Ramon L. Pizarro; Edwin H. Crabtree

(57) ABSTRACT

A wrapping system for wrapping an injured joint, the joint having recessed areas and prominent areas. The system includes stackable resilient sections that are joined to one another by scored areas, the scored areas allowing seperation of each of the resilient section into sections adapted fit in the recessed areas. Each of the resilient section should have an adhesive portion for attaching, in a stacked manner, one resilient section to another resilient section, so that the resulting stacked resilient sections nest in the recessed areas of the injured joint. An elastic wrap strap is used to secure and urge the resilient sections over the injured joint.

5 Claims, 3 Drawing Sheets

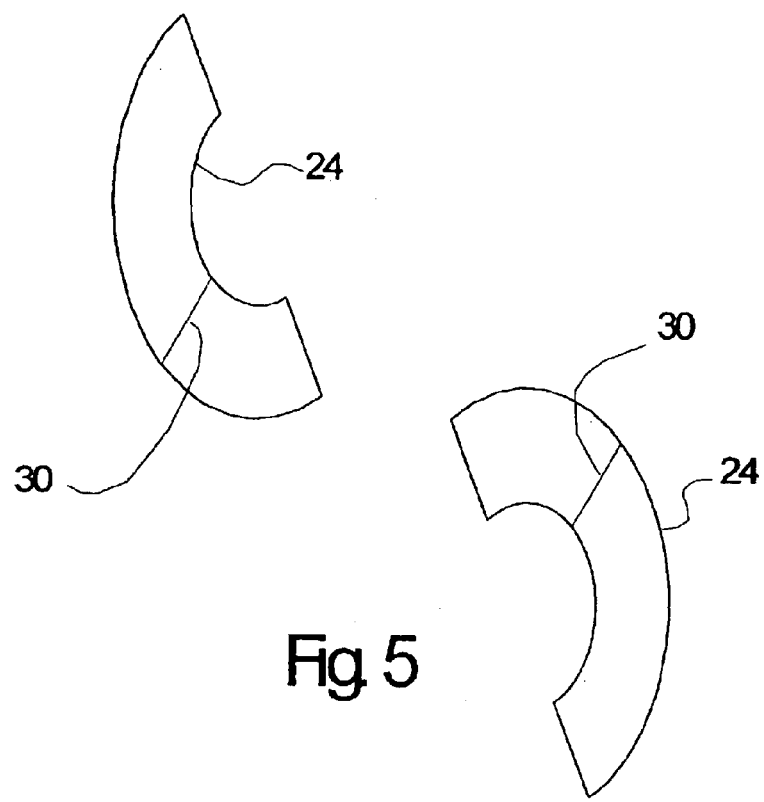
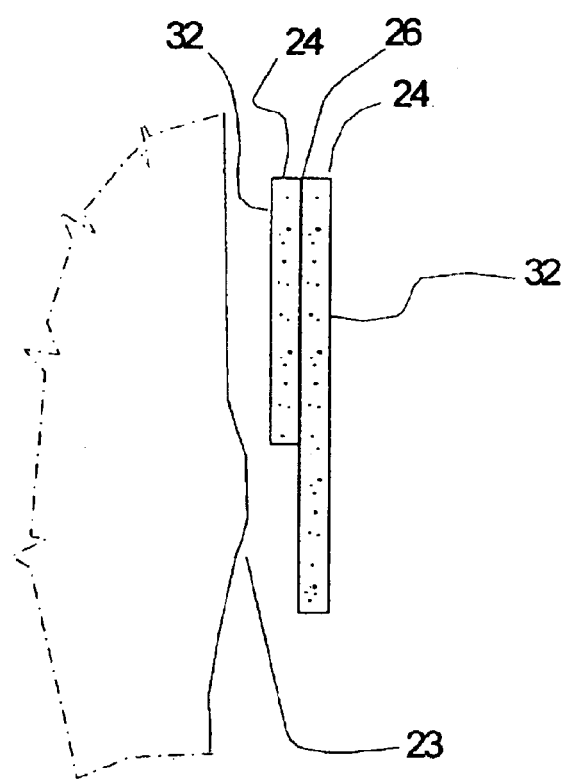

ANKLE WRAPPING SYSTEM

REFERENCE TO RELATED APPLICATIONS

This application is a continuation of my application Ser. No. 09/564,487, filed May 4, 2000, now U.S. Pat. No. 6,533,746, incorporated in its entirety by reference, which claims the benefit of my provisional application having Ser. No. 60/132,635, filed May 5, 1999, now abandoned.

BACKGROUND OF THE INVENTION (a) Field of the Invention

This invention generally relates to a system for wrapping joints, such as an ankle joint or a knee joint on a person's leg. More particularly, but not by way of limitation, to a system that uses an adjustable strap and stackable, adjustable, pressure generating sections, that are used to provide pressure at selected areas under the wrap.

(b) Discussion of Known Art

Sprain type injuries to joint areas, such as ankle joints, knees, elbows, and the like are typically caused by the twisting or hyperextension of the muscles and tissues surrounding the joint. It is well recognized that first aid treatment for these injuries includes providing pressure to the injured joint area. It is particularly important to provide pressure to areas that are likely to fill with blood from torn or injured tissue around the joint. This application of pressure, however, has proven difficult to carry out effectively in the field, since the irregular features or shape of these joints makes it difficult to provide a wrap that provides increased pressure to recessed areas, which are likely to fill with blood, and less pressure to prominent, less irrigated areas, such as the prominent bones of the medial malleolus, or fibula and the tibia.

SUMMARY

It has been discovered that the problems left unanswered by known art can be solved by providing an ankle wrapping system that includes:

A plurality of resilient sections, the sections having an adhesive portion; and

An elastic wrapping strip, the wrapping strip having ends, each end having an adjustable securement mechanism for selectively securing the wrapping strip or strap over the injured joint.

In a preferred embodiment of the invention the resilient sections are foam rubber sections that have been scored at selected locations to allow the user to break away undesired portions of the resilient section, and thus allow tailoring of the resilient section to match the physical characteristics of the injured limb.

It is important to note that the disclosed sections can be stacked to ensure prominence of desired areas of the resilient section. The prominence of portions of the resilient section will ensure that additional pressure is imposed at these locations by the wrapping of the elastic strip, band or strap over the resilient section.

It should also be understood that while the above and other advantages and results of the present invention will become apparent to those skilled in the art from the following detailed description and accompanying drawings, showing the contemplated novel construction, combinations and elements as herein described, and more particularly defined by the appended claims, it should be clearly understood that changes in the precise embodiments of the herein disclosed invention are meant to be included within the scope of the claims, except insofar as they may be precluded by the prior art.

DRAWINGS

The accompanying drawings illustrate preferred embodiments of the present invention according to the best mode presently devised for making and using the instant invention, and in which:

FIG. 5 illustrates the separation of the resilient section along the scored areas to create separate foam portions.

FIG. 6 illustrates placement of the resilient foam portions over the skin (the adhesive backed portion being against the skin) prior to wrapping.

DETAILED DESCRIPTION OF PREFERRED EXEMPLAR EMBODIMENTS

While the invention will be described and disclosed here in connection with certain preferred embodiments, the description is not intended to limit the invention to the specific embodiments shown and described here, but rather the invention is intended to cover all alternative embodiments and modifications that fall within the spirit and scope of the invention as defined by the claims included herein as well as any equivalents of the disclosed and claimed invention.

Figure 1:
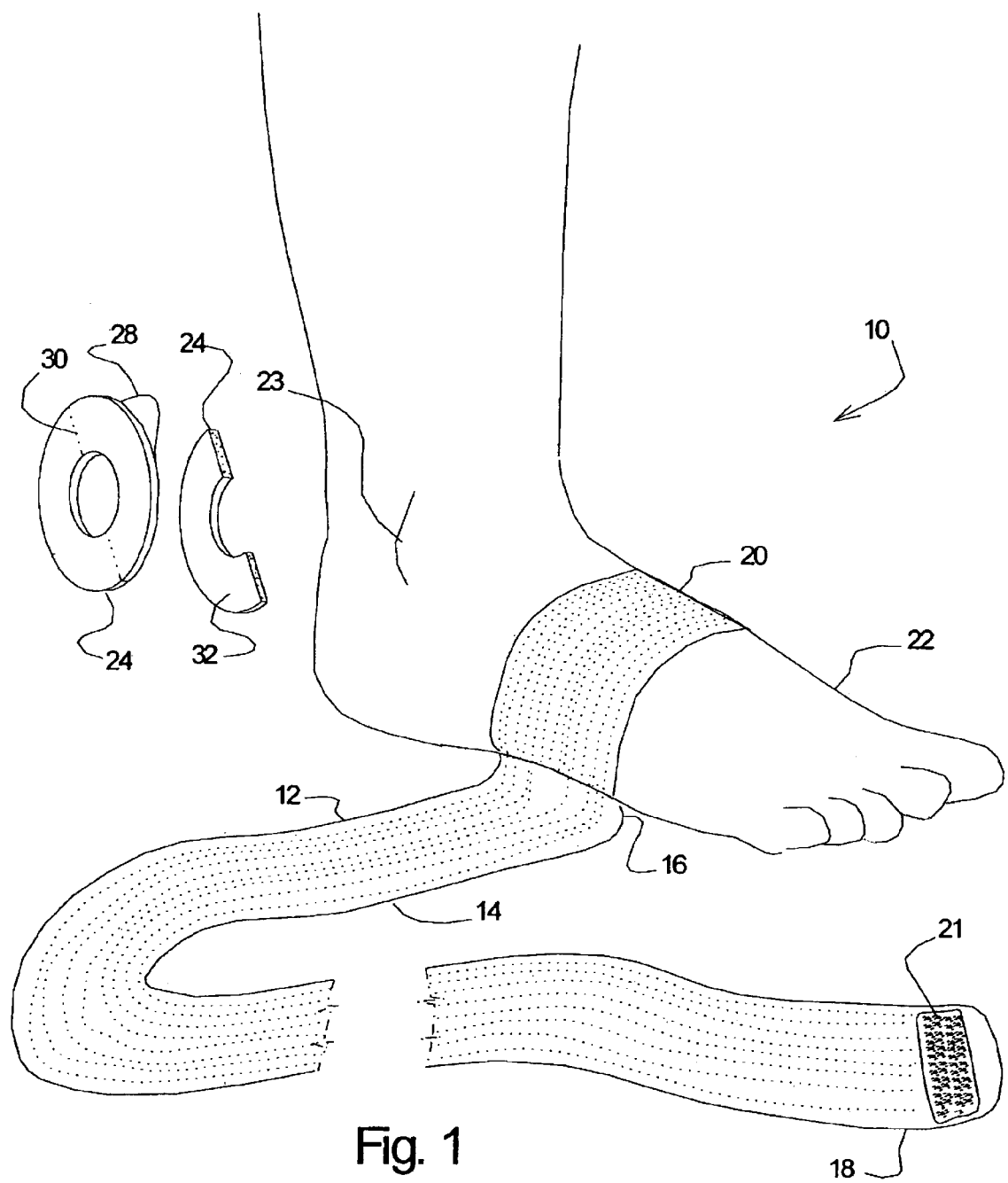
FIG. 1 is a perspective view of an embodiment of the invention used to wrap an inured ankle area.

Turning now to FIG. 1 of the enclosed drawings an ankle support system 10 made in accordance with the principles taught herein has been shown while being administered on a person's leg and foot area. The ankle support system 10 is particularly well suited as a first aid system in tending ankle injuries such as a typical ankle sprain. More specifically, the disclosed system serves as a compression wrap which can be quickly and easily tailored to suit the injury being tended to in the field.

Figure 2:
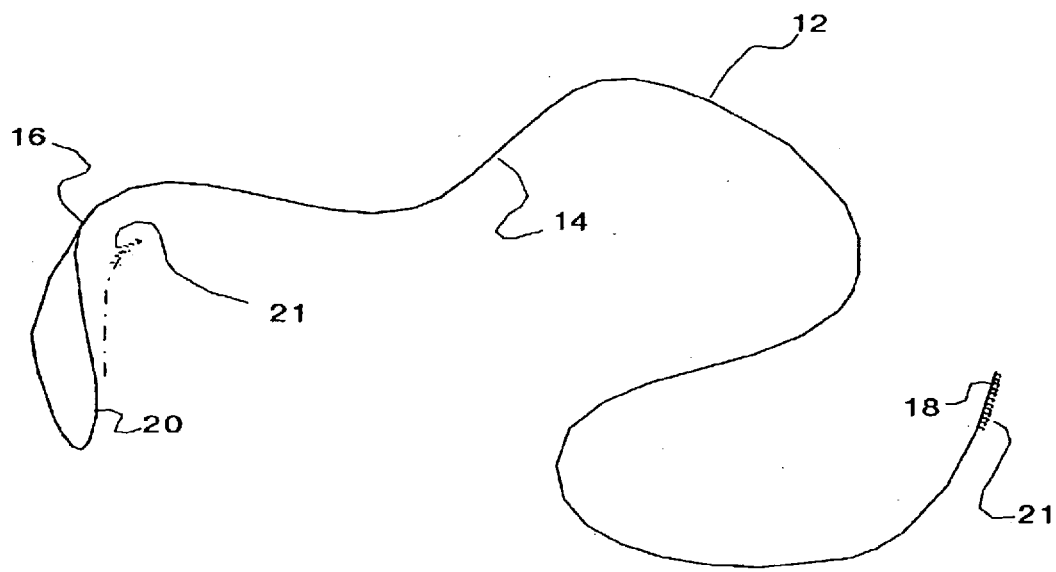
FIG. 2 is a view looking along the edge of the elastic band or strap, and illustrates that while a fixed loop may be incorporated at one end, it is also contemplated that both ends may include hook material that cooperates with the strap or wrapping material to selectively connect or adjust the connection of the strap or band.

As shown in FIGS. 1 and 2, it will be understood that the system 10 includes an elastic wrap 12 which includes a strap shaped body 14 that includes a first end 16 and a second end 18. One of the ends, in the illustrated embodiment the first end 16 includes a loop 20 which has been adapted for receiving a person's foot 22, the wrap 12 is of a length that permits wrapping of the wrap 12 around a person's ankle 23. In a highly preferred embodiment of the invention, the loop 20 is made from the same section of material as the body 14 of the elastic wrap 12. However, it is important to note that it is contemplated that the loop may be fabricated from a separate section of elastic or non-elastic material. Additionally, as shown on FIG. 2, the second end 18 of the body 14 will include a section of adhesive or connector material, which in a preferred embodiment is a section of hook material 21. According to a highly preferred embodiment of the invention, the body 14 will be made of an elastic filament filled fabric made with filaments that will cooperate with the hook material 21 to allow the user to wrap and set the wrap 12 around the injured person's ankle.

Also shown on FIG. 1 is that the system 10 also includes a set of generally rounded, but preferably oval resilient pads 24 having an aperture 25. In a highly preferred embodiment of the invention the resilient pads 24 will be made from a foam rubber composition which will include an adhesive surface 26. Preferably, the adhesive surface 26 will include a peel away cover 28 that will allow the resilient pads 24, or sections thereof, to adhere to one another or to adhere to the person's skin as desired.

Figure 3:
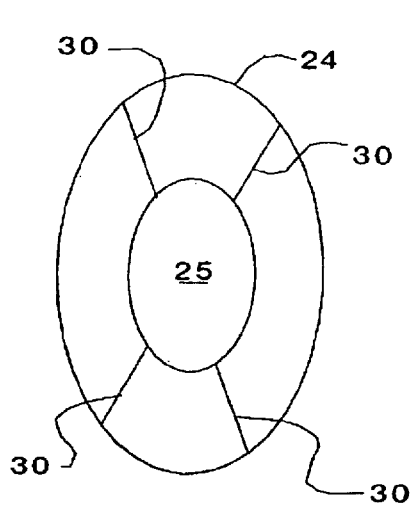
FIG. 3 is a top, plan view of an embodiment of the resilient sections used with the disclosed invention.
Figure 4:
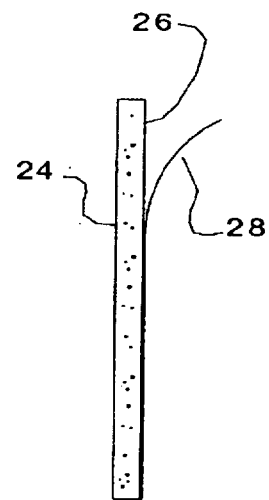
FIG. 4 is a side view of the embodiment illustrated in FIG. 3.

Turning now to FIGS. 2–4 it will be understood that the disclosed pads 24 will preferably include scored areas 30 that will allow the user to break the pads 24 into sections 32. These sections 32 will allow the user to form a stack of pad sections that will include thick sections, formed from several sections 32 stacked together, and thinner sections with few stacked sections 32 of pad 24. This variation in the thickness of the stack of sections is particularly useful in providing the precise needed pressure to the areas of the ankle which are prone to filling and swelling due to bleeding and edema around the injured ankle. It has been discovered that this tailored pad allows the user to provide an even distribution of pressure from the wrap 12 to the injured area of the ankle. The uniform distribution of the pressure prevent the fluids that are causing the swelling from migrating to an area with little or reduced pressure as compared to the other areas under the wrap 12.

Turning now to FIGS. 5 and 6 it will be understood that the stacking and adjustments to the overall thickness of the stack up will be accomplished by breaking off sections of the foam pads 24 along the scored area 30 and adhering the sections to one another. The finished stack would then generally conform to the anatomical contours of the injured ankle. By filling the recesses and following the contours with the foam of the resilient pads 24 one provides an even, raised area which can then be covered by the wrap 12 to provide even pressure over the injured section of the foot.

Additionally, it will be understood that the disclosed invention will serve as an exercise device to exercise the muscles of the ankle and foot. To use the invention as an exercise device, a user would simply insert his foot into the loop 20, while holding the length of the elastic body 14 fixed relative to the foot. Then, the user would flex his foot to impart resistance against the foot by stretching the elastic body 14 as the user flexes his foot.

Thus it can be appreciated that the above described embodiments are illustrative of just a few of the numerous variations of arrangements of the disclosed elements used to carry out the disclosed invention. Moreover, while the invention has been particularly shown, described and illustrated in detail with reference to preferred embodiments and modifications thereof, it should be understood that the foregoing and other modifications are exemplary only, and that equivalent changes in form and detail may be made without departing from the true spirit and scope of the invention as claimed, except as precluded by the prior art.

What is claimed is:

1. A wrapping system for wrapping an injured joint, the joint having recessed areas and prominent areas, the system comprising:

a plurality of stackable resilient sections that are joined to one another by scored areas, the scored areas allowing separation of each of the resilient section into sections adapted fit in the recessed areas, each of the resilient sections having an adhesive portion for attaching, in a stacked manner, one resilient section to another resilient section, so that the resulting stacked resilient sections nest in the recessed areas of the injured joint; and an elastic wrap strap, the wrap strap having ends, the elastic wrap strap securing the resilient sections over the injured joint.

2. A wrapping system according to claim 1 wherein the stackable resilient sections joined to one another by scored areas are generally oval.

3. A method for treating an injured joint by filling and accommodating contoured or recessed areas of a joint to match the physical characteristics of the joint with the use of a section of elastic material such as an elastic wrap strap, the method comprising:

providing a resilient pad having an adhesive surface covered with a peel-away cover that conceals the adhesive surface until ready for use, the resilient pad further having a plurality of scored areas for selectively separating the pad into a plurality of resilient sections, each of the resilient sections having an adhesive portion;

filling the contoured areas of the joint by separating the least one of the resilient sections and positioning the resilient section over the contoured or recessed area of the injured joint; and urging the resilient section against the contoured areas with the elastic wrap, so that the elastic wrap provides substantially uniform pressure to recessed and contoured areas of the joint.

4. A method according to claim 3, wherein the resilient pad is generally oval and the resilient sections are scored in a generally radial manner to allow separation of the resilient sections for selective stacking of parts of the resilient sections on top of one another.

5. A method according to claim 4 wherein the resilient pad is generally O-shaped.

* * * * *